United States Patent [19]

Mardorf et al.

[11] Patent Number: 4,624,658
[45] Date of Patent: Nov. 25, 1986

[54] DISTENSIBLE SYRINGE AND SENSOR FOR INJECTORS

[75] Inventors: Robert Mardorf; Friedrich von der Haar, both of Melsungen, Fed. Rep. of Germany

[73] Assignee: Intermedicat GmbH, Emmenbrucke, Switzerland

[21] Appl. No.: 667,997

[22] Filed: Nov. 5, 1984

[30] Foreign Application Priority Data

Nov. 9, 1983 [DE] Fed. Rep. of Germany ....... 3340511

[51] Int. Cl.$^4$ .............................................. A61M 5/20
[52] U.S. Cl. ..................................... 604/121; 604/154; 128/DIG. 1
[58] Field of Search ............... 604/154, 155, 131, 118, 604/121; 128/DIG. 1

[56] References Cited

U.S. PATENT DOCUMENTS

| 2,742,901 | 4/1956 | Krauthamer | 604/154 X |
| 4,030,497 | 6/1977 | Binard et al. | 604/121 |
| 4,465,474 | 8/1984 | Mardorf et al. | 604/154 |

FOREIGN PATENT DOCUMENTS 372943 4/1923 Fed. Rep. of Germany ...... 604/153

Primary Examiner—Stephen C. Pellegrino
Attorney, Agent, or Firm—Kenyon and Kenyon

[57] ABSTRACT

A syringe for an injector utilizes a cylinder having a deformable wall portion in the outlet end. Excessive pressure within the syringe cylinder, or contact with the syringe piston at the end of its stroke distends the deformable wall portion of the cylinder, actuating a sensor which provides a signal.

11 Claims, 6 Drawing Figures

4,624,658

DISTENSIBLE SYRINGE AND SENSOR FOR INJECTORS

BACKGROUND OF THE INVENTION

1. Field of the Invention

The present invention relates generally to syringes for injectors, and more particularly to such syringes which distend under pressure, actuating a sensor.

2. Description of the Prior Art

In the medical field, prior art injectors are known (U.S. Pat. No. 4,465,475) which permits long-term infusions by the slow and continuous squeezing of a syringe. The syringe is fixed by its cylinder to a holder of the injector. A slide pushes the piston rod of the syringe forward so that the infusion solution contained in the syringe is steadily discharged from the cylinder at a predetermined selectable rate. When an obstruction occurs in the fluid line that leads from the syringe outlet to the patient, or when the piston reaches its forwardmost position and strikes against the end of the cylinder, an alarm is triggered which indicates to the attendants that the infusion has been disturbed, or that the cylinder has been emptied and may require replacement. The holder to which the cylinder is attached is designed to move longitudinally. This motion is inhibited by a spring. When the fluid line leading from the cylinder to the patient is obstructed, or when the piston strikes the end of the cylinder, the holder is displaced by the force exerted upon the cylinder, counter to the action of the spring, whereby a micro-switch is actuated which triggers the alarm.

This apparatus of the prior art entails certain disadvantages. The mechanism described above for sensing pressure in the cylinder is relatively complicated, requiring that the cylinder holder be moveably attached to the injector. Further, friction between the piston and cylinder affects the triggering point of the alarm. Since this friction may vary from one syringe to another, there is no assurance that the alarm will be triggered by the same fluid pressure in a cylinder.

If excessive pressure in the cylinder were determined by measuring the current drain of the injector motor which operates the syringe piston, variations in syringes would again engender inaccuracies.

SUMMARY OF THE INVENTION

An object of the invention is to provide a disposable syringe for an injector, wherein overload of the syringe due to pressure or force in the cylinder can be inexpensively determined.

In accordance with the invention, the cylinder of the syringe comprises a deformable wall portion which distends from fluid pressure or direct contact with the piston, and which thereby actuates a position sensor on the injector. Thus, the syringe can be fixed by a holder which is firmly coupled to the housing of the injector, and need not be displaceable. Also, the position sensor can be firmly coupled to the housing of the injector, allowing, of course, for possible adjustment of the position of the sensor.

In a preferred embodiment of the invention the deformable wall portion comprises the outlet end wall (breast) of the syringe cylinder. The cylinder breast is particularly suitable for the deformable wall portion; since, it is located at the outlet end of the cylinder, and upon deformation neither affects the inside diameter of the cylinder, nor impairs the piston seal.

The deformable wall portion may alternatively be disposed in the longitudinal wall of the cylinder. When the fluid pressure is excessive, the portion distends outwardly, actuating the position sensor. The deformable wall portion may extend into the interior of the cylinder so that upon contact with the piston during forward motion, the portion is pushed outward. Any flexible cross-sectional restriction of the cylinder is suitable for this purpose. If the sensor is to respond only to fluid pressure, and not to the position of the piston, the deformable wall portion may have any desired form, if it expands outwardly under excessive fluid pressure.

The position sensor may simply comprise a switch which is actuated by the deformable wall portion. However, a position sensor may be utilized which furnishes an output signal that is proportional to the distension of the deformable wall portion. In this fashion, a preliminary alarm can be given, or the fluid pressure, or piston position can be indicated, permitting attendants to monitor the values before an acute condition is signalled.

BRIEF DESCRIPTION OF THE DRAWINGS

FIG. 3 is a cross-sectional view of a cylinder of the syringe with a piston disposed therein, a deformable portion disposed in the longitudinal wall of the cylinder, and a sensing pin coupled to a position sensor.

FIG. 4 is a cross-sectional view of the apparatus of FIG. 3 upon actuation of the position sensor in response to excessive fluid pressur in the cylinder.

FIG. 5 is a cross-sectional view of the apparatus of FIG. 3 wherein the deformable portion disposed in the longitudinal wall of the cylinder extends into the interior of the cylinder.

FIG. 6 is a cross-sectional view of the apparatus of FIG. 5 upon actuation of the position sensor in response to contact of the piston with the defomable wall portion.

Idential numberal in different figures refer to identical elements.

DESCRIPTION OF THE PREFERRED EMBODIMENTS

The present invention entails a disposable syringe for injectors, having a defomable wall portion which distends in response to excessive fluid pressure or contact with the cylinder piston, to actuate a sensor.

Figure 1:
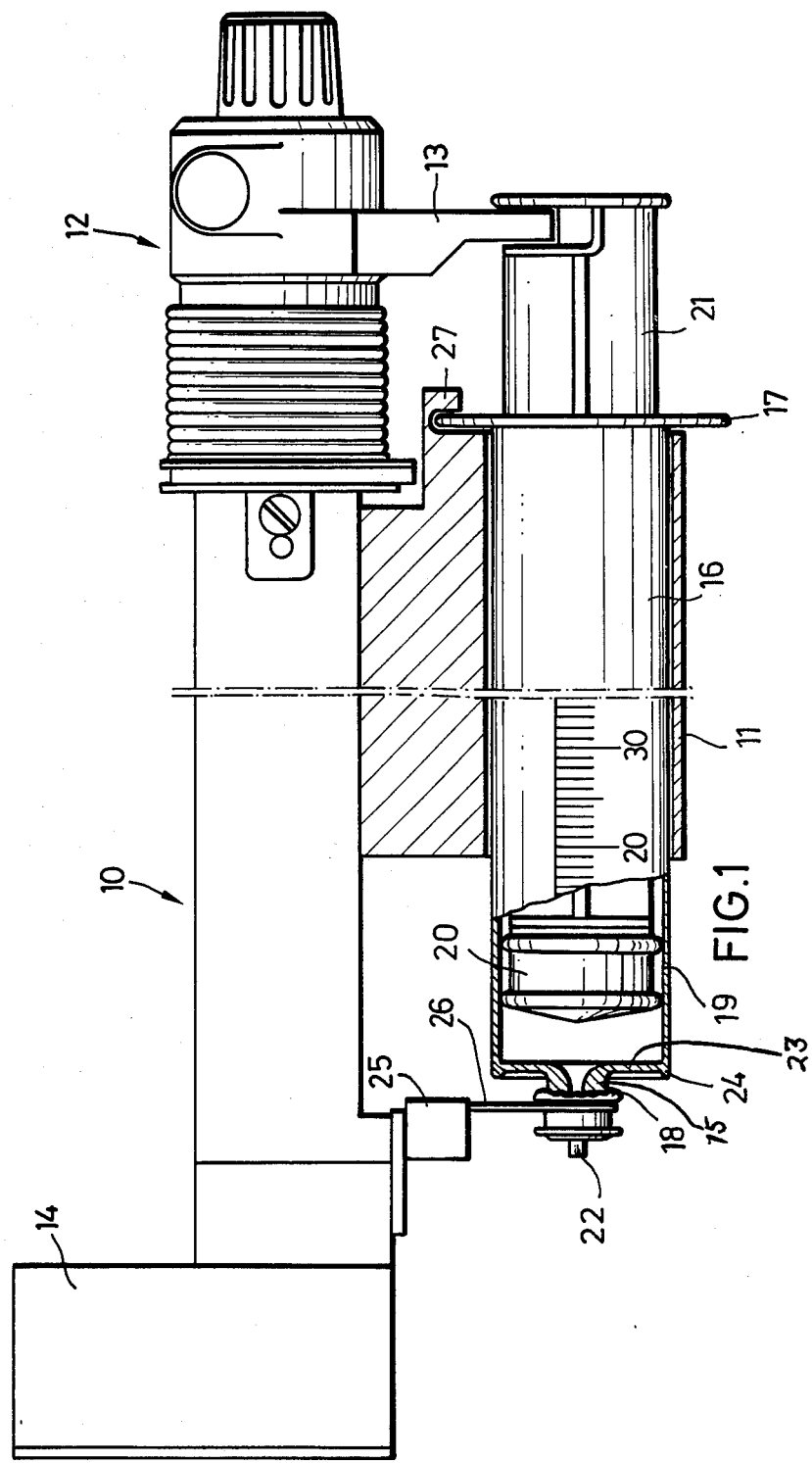
FIG. 1 is a side view, partially cut-away, of an injector with a syringe suspended therefrom, shortly before actuation of a position sensor.

Referring to FIG. 1, an injector comprises an elongated tubular housing 10, to whose underside a first holder 11 having an opening in one end is firmly coupled. A slide 12 is disposed in the housing 10. The slide 12 projects from the free end of the housing 10, and carries a second holder 13 which extends downward. A motor 14 fixed to the housing 10 drives the slide 12. A cylinder 19 of a syringe 16 is disposed within the first holder 11. The syringe 16 preferably comprises plastic. A flange 17 on the rear end of the cylinder 19 is disposed at the back of the holder 11. The flange 17 is held by a lug 27 of the holder 11, so that the cylinder 19 is fixed along the longitudinal axis of the holder 11.

The syringe 16 comprises a piston 20, displaceable within the cylinder 19. A flange 18 is disposed at a neck 15 of the cylinder 19. A piston rod 21, coupled to the piston 20, extends from the rear end of the cylinder 19, and is coupled to the second holder 13.

A tube, not shown, is coupled to a nipple 22 disposed on the neck 15, and extends from the syringe 16 to a patient. At the beginning of an infusion, the piston 20 is situated proximate the rear end of the cylinder 19. The motor 14 drives the slide 12 so that the piston 20 is slowly pushed forward in the cylinder 19, thereby discharging the contents of the syringe 16 through the nipple 22.

The outlet end wall of the cylinder 19 is fashioned as a deformable wall portion 23. The deformable wall portion 23 may entail, for example, a thinner wall thickness than the other wall portions of the cylinder 19. The deformable wall portion 23, which extends radially outward from the central longitudinal axis of the cylinder 19, meets at its outer edge the longitudinal wall of the cylinder 19 forming a rim 24, and borders with its inner edge the relatively thick wall of the neck 15. Thus, the deformable wall portion 23 is bounded on the outside by the rim 24, and on the inside by the neck 15.

Figure 2:
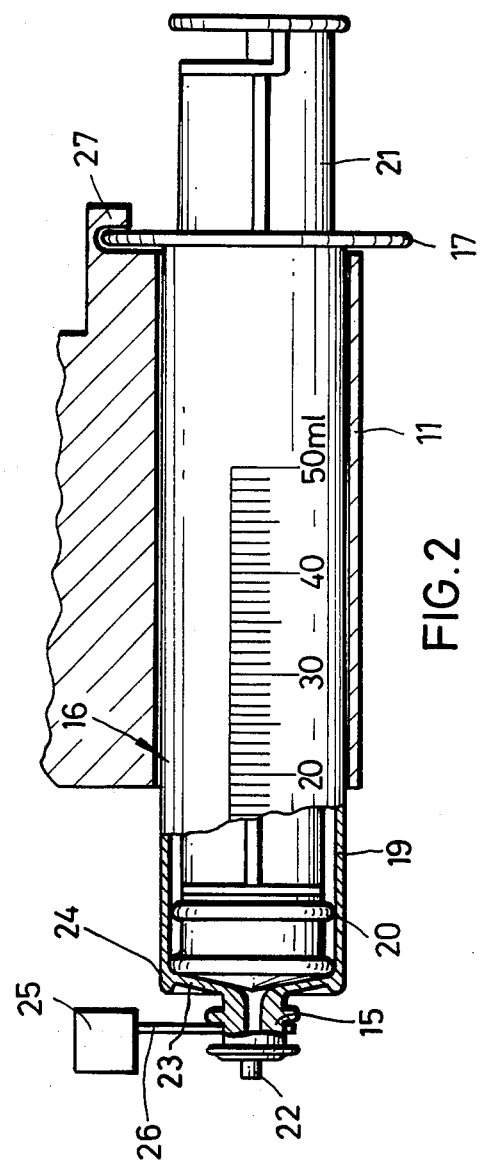
FIG. 2 is a side view, partially cut away, of the syringe of FIG. 1 upon actuation of the position sensor.

A position sensor 25 is attached to the housing 10 or to the holder 11. A forked sensing pin 26, coupled to the position sensor 25, contacts the area of the neck 15 in front of the flange 18. Referring to FIG. 2, when the deformable wall portion 23 is distended by excessive fluid pressure in the cylinder 19, or by direct contact with the piston 20, the neck 15 is moved forward, displacing the sensing pin 26. The position sensor 25 may be set to provide an alarm in response to a predetermined displacement of the sensing pin 26. The position sensor 25, in this case, may simply comprise a switch In this fashion, an attendant may be alerted to either excessive fluid pressure in the cylinder 19, or to the piston 20 having made contact with the deformable wall portion 23 after completing its stroke. Also, since the distension of the deformable wall portion 23 is proportional to the fluid pressure in the cylinder 19, the position sensor 25 may be designed to provide an electrical signal whose magnitude is proportional to the resulting displacement of the sensing pin 26. In this fashion, a preliminary alarm can be given, or the pressure in the cylinder 19 continuously indicated, before an emergency level is reached.

Referring to FIGS. 3 and 4, a deformable wall portion 30 may, alternatively, be disposed in the longitudinal wall of the cylinder 19, with an associated sensing pin 32 and position sensor 33. Referring to FIGS. 5 and 6, further a deformable wall portion 35 may extend into the interior of the cylinder 19 so that upon contact with the piston 20 during forward motion, the wall portion is pushed outward. Any flexible cross-sectional restriction of the cylinder 19 is suitable for this purpose.

If the sensor is to respond only to fluid pressure in the cylinder 19, and not to the position of the piston 20, the deformable wall portion may have any desired form which expands outwardly under excessive fluid pressure.

While the invention has been described in its preferred embodiments, it is to be understood that the words which have been used are words of description rather than limitation and that changes may be made within the purview of the appended claims without departing from the true scope and spirit of the invention in its broader aspects.

We claim:

1. A syringe for injectors, comprising:
   a cylinder having a deformable wall portion, a longitudinal wall, a first and a second end, an outlet end wall dsposed at said first end, and a neck disposed on said outlet end wall;
   a piston, disposed in said cylinder; and,
   means, disposed in contact with a region of said cylinder which moves upon distension of said deformable wall portion, for providing an output signal proportional to said distension of said deformable wall portion.

2. An apparatus as in claim 1 wherein said proportional output signal providing means comprises a sensing pin, disposed in contact with said region of said cylinder which moves upon distension of said deformable wall portion; and, a position sensor, coupled to said sensing pin.

3. An apparatus as in claim 1 wherein said deformable wall portion is disposed in said outlet end wall, and wherein said proportional output signal providing means is disposed in contact with said neck of said cylinder.

4. An apparatus as in claim 3 wherein said proportional output signal providing means comprises a sensing pin, disposed in contact with said neck of said cylinder; and, a position sensor, coupled to said sensing pin.

5. An apparatus as in claim 1 wherein said deformable wall portion is disposed in said longitudinal wall, and wherein said proportional output signal providng means is disposed in contact with said deformable wall portion.

6. An apparatus as in claim 5 wherein said proportional output signal providing means comprises a sensing pin, disposed in contact with said deformable wall portion; and, a position sensor, coupled to said sensing pin.

7. A syringe for injectors, comprising:
   a cylinder having a longitudinal wall, a deformable wall portion disposed in said longitudinal wall, a first and a second end, an outlet end wall disposed at said first end, and a neck disposed on said outlet end wall; and,
   a piston disposed in said cylinder,
   said deformable wall portion extending into an interior of said cylinder in a path of said piston so that upon contact with said piston said deformable wall portion is distended.

8. An apparatus as in claim 7 further comprising means, disposed in contact with said deformable wall portion, for providing an output signal in response to distension of said deformable wall portion.

9. An apparatus as in claim 8 wherein said output signal providing means comprises a sensing pin, disposed in contact with said deformable wall portion; and, a position sensor, coupled to said sensing pin.

10. An apparatus as in claim 8 wherein said output signal providing means comprises means, disposed in contact with said deformable wall portion, for providing an output signal proportional to distension of said deformable wall portion.

11. An apparatus as in claim 10 wherein said proportional output signal providing means comprises a sensing pin, disposed in contact with said deformable wall portion; and, a position sensor, coupled to said sensing pin.

* * * * *